United States Patent [19]

Beasley Jr. et al.

[11] Patent Number: 6,071,902
[45] Date of Patent: Jun. 6, 2000

[54] METHOD FOR TREATING EXCESSIVE AGGRESSION

[75] Inventors: Charles M Beasley Jr., Indianapolis; Pierre V Tran, Carmel, both of Ind.

[73] Assignee: Eli Lilly and Company, Indianapolis, Ind.

[21] Appl. No.: 08/952,919

[22] PCT Filed: Dec. 4, 1996

[86] PCT No.: PCT/US96/19573

§ 371 Date: Nov. 25, 1997

§ 102(e) Date: Nov. 25, 1997

[87] PCT Pub. No.: WO97/33584

PCT Pub. Date: Sep. 18, 1997

[51] Int. Cl.[7] .................................................. A61K 31/381
[52] U.S. Cl. ................................................................ 514/220
[58] Field of Search ................................................ 514/220

[56] References Cited

U.S. PATENT DOCUMENTS 4,595,535   6/1986   Vlattas .
5,229,382   7/1993   Chakrabarti et al. .

*Primary Examiner*—Raymond Henley, III
*Attorney, Agent, or Firm*—Arleen Palmberg; Macharro Vorndran Jones

[57] ABSTRACT

The invention provides a method for treating extreme aggression in a mammal comprising administering an effective amount of olanzapine, or a pharmaceutically acceptable salt or solvate thereof, to the mammal.

6 Claims, No Drawings

METHOD FOR TREATING EXCESSIVE AGGRESSION

This is a 371 of PCT/US96/19573 filed Dec. 4, 1996.

This invention provides a method for using 2-methyl-4-(4-methyl-1-piperazinyl)-10H-thieno[2,3-b][1,5]benzodiazepine, (hereinafter referred as "olanzapine"), for the treatment of excessive aggression.

Excessive agression can be a problem for institutionalized patients and may be associated with violent suicides. Extreme aggressiveness can be harmful to the individual prone to extreme aggressivenes, may be detrimental to relationships and family members interacting with the individual, and may complicate the management of patients or prisoners in the institutional setting.

Studies of animals and human beings suggest that 5-HT serves a critical role in aggression and impulsivity. Several human studies report a correlation between low cerebrospinal fluid 5-HIAA and violent suicides. Therefore, extreme aggression appears to be associated with abnormalities in 5-HT. Goodman and Gillman, *The Parmacololgical Basis of Therapeutics,* 257 (9th Ed. McGraw-Hill, New York, 1996). However, there is a need for new treatments that can manage extreme aggression in a safe and ethical manner.

It is known that olanzapine can provide antipsychotic activity and is currently undergoing investigation for this purpose. Olanzapine is a known compound and described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety. However, olanzapine was not known to be useful for the treatment of excessive aggression. Applicants have discovered that olanzapine can be useful for the treatment of extreme aggression. Olanzapine could address a long felt need for treatments which provides a favorable safety profile and effectively provides relief for the patient or individual suffering from extreme aggression.

The presently claimed invention provides a method for treating extreme aggression, comprising administering an effective amount of olanzapine or a pharmaceutically acceptable salt thereof to a patient in need of such treatment.

The present invention provides a method for treating excessive aggression in a mammal, wherein the mammal is not clinically diagnosed as suffering from a psychotic condition.

Olanzapine is of the formula

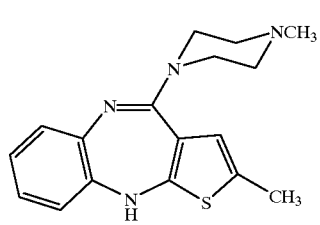

(I)

or an acid addition salt thereof.

It is especially preferred that olanzapine will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper $K_\alpha$ radiation source of wavelength, $\lambda=1\cdot541$ Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the Form II polymorph should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and $I/I_1$ represents the typical relative intensities:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |

-continued

| d | $I/I_1$ |
|---|---|
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_\alpha$ of wavelength $\lambda=1.541$ Å. The interplanar spacings in the column marked "d" are in Angstroms. The typical relative intensities are in the column marked "$I/I_1$".

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "extreme aggression" shall refer to a condition characterized by aggression that is so extreme that it interferes with the individual's daily functions, relationships, and may threaten the safety of the individual, for example in a situation in which violent suicide is contemplated. The extreme aggression which may be treated using the method claimed herein shall be independent of a psychotic condition and not directly related to the consumption of a drug or other substance.

The results of pharmacological studies show that olanzapine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, olanzapine is active at the 5-HT-2 receptor and 5-HT1C receptor. The complex pharmacological profile of the compound provides a medicament which can be useful for the treatment of extreme aggression.

The usefulness of the compound for treating extreme aggression can be supported by the following studies as described.

Clinical observations.

A double-blind multicenter clinical trial was designed to assess the safety and efficacy of olanzapine. Patients were randomized to olanzapine or placebo. The results of the study suggest that olanzapine can be useful for the treatment of excessive aggression.

Olanzapine is effective over a wide dosage range, the actual dose administered being dependent on the condition being treated. For example, in the treatment of adult humans, dosages of from 5 to 20 mg per day may be used. A once a day dosage is normally sufficient, although divided doses may be administered. For treatment of extreme aggression, a dose range of from 5 to 20 mg per day is suitable. Radiolabelled olanzapine, can be detected in the saliva and thus the compound can potentially be monitored in patients to assess compliance.

A preferred formulation of the invention is a solid oral formulation comprising from about 1 to about 20 mg or 1 to 10 mg of olanzapine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

Olanzapine will normally be administered orally or by injection and, for this purpose, it is usually employed in the form of a pharmaceutical composition.

Accordingly, pharmaceutical compositions comprising olanzapine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 5 to 20 mg, of the active ingredient.

Olanzapine can be useful for the management of excessive aggression for veterinary science purposes. Most preferredly, the veterinary patient is a mammal. For animal health purposes, olanzapine can be administered as a feed additive.

The materials for the present invention can be purchased or prepared by a variety of procedures well known to those of ordinary skill in the art. Olanzapine can be prepared as described by Chakrabarti in U.S. Pat. No. 5,229,382 ('382), herein incorporated by reference in its entirety. Further, the following preparations illustrate a method for preparing of the especially preferred Form II olanzapine polymorph.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

Preparation 1

Technical Grade olanzapine

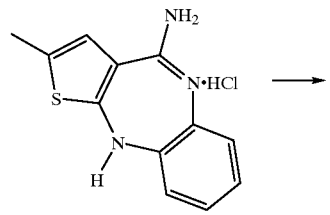

Intermediate 1

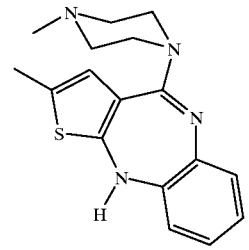

In a suitable three neck flask the following was added:

Dimethylsulfoxide (analytical): 6 volumes

Intermediate 1: 75 g

N-Methylpiperazine (reagent): 6 equivalents

Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until ≦5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

Preparation 2

Form II olanzapine polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency≧97%, total related substances<0.5% and an isolated yield of>73%.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

What is claimed is:

1. A method for treating excessive aggression in a mammal, wherein the mammal is not clinically diagnosed with a psychotic condition comprising administering an effective amount of olanzapine, or a pharmaceutically acceptable salt or solvate thereof, to such mammal.

2. A method of claim 1 wherein the effective amount is from about 2.5 to about 30 mg per day.

3. A method of claim 1 wherein the olanzapine is Form II olanzapine polymorph.

4. A method of claim 1 wherein the mammal is a human.

5. A method of claim 2 wherein the mammal is a human.

6. A method of claim 3 wherein the mammal is a human.

* * * * *